(12) United States Patent
Dasbach et al.

(10) Patent No.: US 9,566,118 B2
(45) Date of Patent: Feb. 14, 2017

(54) NEEDLE ASSEMBLY MAGAZINE

(75) Inventors: Uwe Dasbach, Frankfurt am Main (DE); Verena Hofmann, Frankfurt am Main (DE); Gunnar Jung, Mainz (DE); Peter Nober, Rommersheim (DE); Leo Zeimetz, Buttelborn (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 314 days.

(21) Appl. No.: 14/113,865

(22) PCT Filed: Apr. 17, 2012

(86) PCT No.: PCT/EP2012/057002
§ 371 (c)(1),
(2), (4) Date: Oct. 25, 2013

(87) PCT Pub. No.: WO2012/146509
PCT Pub. Date: Nov. 1, 2012

(65) Prior Publication Data
US 2014/0048555 A1    Feb. 20, 2014

(30) Foreign Application Priority Data
Apr. 28, 2011   (EP) .................................. 11164067

(51) Int. Cl.
*A61B 19/02*   (2006.01)
*A61M 5/00*   (2006.01)
*B65D 85/24*   (2006.01)

(52) U.S. Cl.
CPC ....... *A61B 19/0262* (2013.01); *A61B 50/3001* (2016.02); *A61M 5/002* (2013.01); *B65D 85/24* (2013.01); *B65D 2209/00* (2013.01)

(58) Field of Classification Search
CPC ... A61B 19/0262; B65D 2209/00; G07F 11/04
See application file for complete search history.

(56) References Cited

U.S. PATENT DOCUMENTS

| | | | | |
|---|---|---|---|---|
| 3,502,244 A | * | 3/1970 | Irvin | .............................. 221/63 |
| 3,809,287 A | * | 5/1974 | Muller-Scherak | .............. 221/66 |
| 3,941,244 A | | 3/1976 | Braginetz | |

(Continued)

FOREIGN PATENT DOCUMENTS

| | | |
|---|---|---|
| EP | 0697222 | 2/1996 |
| WO | 01/87387 | 11/2001 |
| WO | 03/080467 | 10/2003 |

OTHER PUBLICATIONS

International Search Report for Int. App. No. PCT/EP2012/057002, completed May 11, 2012.

*Primary Examiner* — Gene Crawford
*Assistant Examiner* — Kelvin L Randall, Jr.
(74) *Attorney, Agent, or Firm* — Fish & Richardson P.C.

(57) ABSTRACT

Described is a needle assembly magazine comprising of a housing adapted to contain a plurality of needle assemblies and a slider movably disposed within the housing. The housing has a first opening providing access to an unused needle assembly and a second opening for receiving into the housing a used needle assembly. The slider separates the housing into a first region for unused needle assemblies and a second region for used needle assemblies. Movement of the slider advances the unused needle assemblies within the housing toward the first opening.

9 Claims, 4 Drawing Sheets

(56) References Cited

U.S. PATENT DOCUMENTS

| | | | |
|---|---|---|---|
| 4,848,569 A | | 7/1989 | Leishman |
| 5,084,028 A | * | 1/1992 | Kennedy et al. .............. 604/192 |
| 7,014,062 B2 | * | 3/2006 | Parris et al. .................... 221/34 |
| 7,104,400 B2 | * | 9/2006 | Kiehne ......................... 206/366 |
| 2002/0014430 A1 | | 2/2002 | Groth |
| 2003/0015444 A1 | | 1/2003 | Molin et al. |
| 2011/0060292 A1 | * | 3/2011 | Schraga ........................ 604/240 |
| 2012/0041390 A1 | * | 2/2012 | Spool et al. ................... 604/240 |
| 2015/0011974 A1 | * | 1/2015 | Schraga ........................ 604/506 |

* cited by examiner

NEEDLE ASSEMBLY MAGAZINE

CROSS REFERENCE TO RELATED APPLICATIONS

The present application is a U.S. National Phase Application pursuant to 35 U.S.C. §371 of International Application No. PCT/EP2012/057002 filed Apr. 17, 2012, which claims priority to European Patent Application No. 11164067.8 filed Apr. 28, 2011. The entire disclosure contents of these applications are herewith incorporated by reference into the present application.

TECHNICAL FIELD

The invention relates to a needle assembly magazine for storing needle assemblies.

BACKGROUND

Patients suffering from diseases like diabetes have to frequently self-administer injections. Injection devices like auto-injectors or pen injectors have been developed to facilitate self-administering injections. Typically, such injection devices can be used for several injections and are refitted with sterile injection needle assemblies to minimize the risk of infections.

Conventionally, the needle assemblies are packaged in a box or container, which not easily transported. There are some examples of needle assembly storage devices, e.g., U.S. Pat. No. 4,848,569, US 2002014430 A1, and US 2003015444 A1. However, there remains a need for a portable device for storing the needle assemblies. Such a device would provide additional usefulness if used needle assemblies could also be stored in the device, e.g., if there is not ready access to a disposal unit for needle devices.

SUMMARY

It is an object of the present invention to provide an improved means for storing and disposing needle assemblies.

Described is a needle assembly magazine comprising a housing adapted to contain a plurality of needle assemblies and a slider movably disposed within the housing. The housing has a first opening providing access to an unused needle assembly and a second opening for receiving into the housing a used needle assembly. The slider separates the housing into a first region for unused needle assemblies and a second region for used needle assemblies. Movement of the slider advances the unused needle assemblies within the housing toward the first opening.

In an exemplary embodiment, the housing is elongated and comprises a first portion, a second portion, a hinge coupling the first portion to the second portion, and a lock for selectively locking the first portion to the second portion. The first opening may be formed at a first terminal end of the housing and the second opening may be formed at a second terminal end of the housing. At least one of the first opening and the second opening may be selectively covered by a door. A guide for an injection device may be formed around at least one of the first opening and the second opening.

In an exemplary embodiment, a holder may be disposed within the housing adjacent the second opening. The holder may receive the used needle assembly and be movable between a first position and a second position. A lever may be use for moving the holder within the housing from the first to the second position, and a hook extending into an interior of the housing may be used to separate the used needle assembly from the holder when the holder is moved between the first and second positions. The holder may comprise a pair of arms adapted to at least partially encircle the used needle assembly.

In an exemplary embodiment, a first visual indicator is disposed on the housing to indicate that the first opening provides access to the unused needle assemblies, and a second visual indicator is disposed on the housing to indicate that the second opening is for receiving the used needle assemblies.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
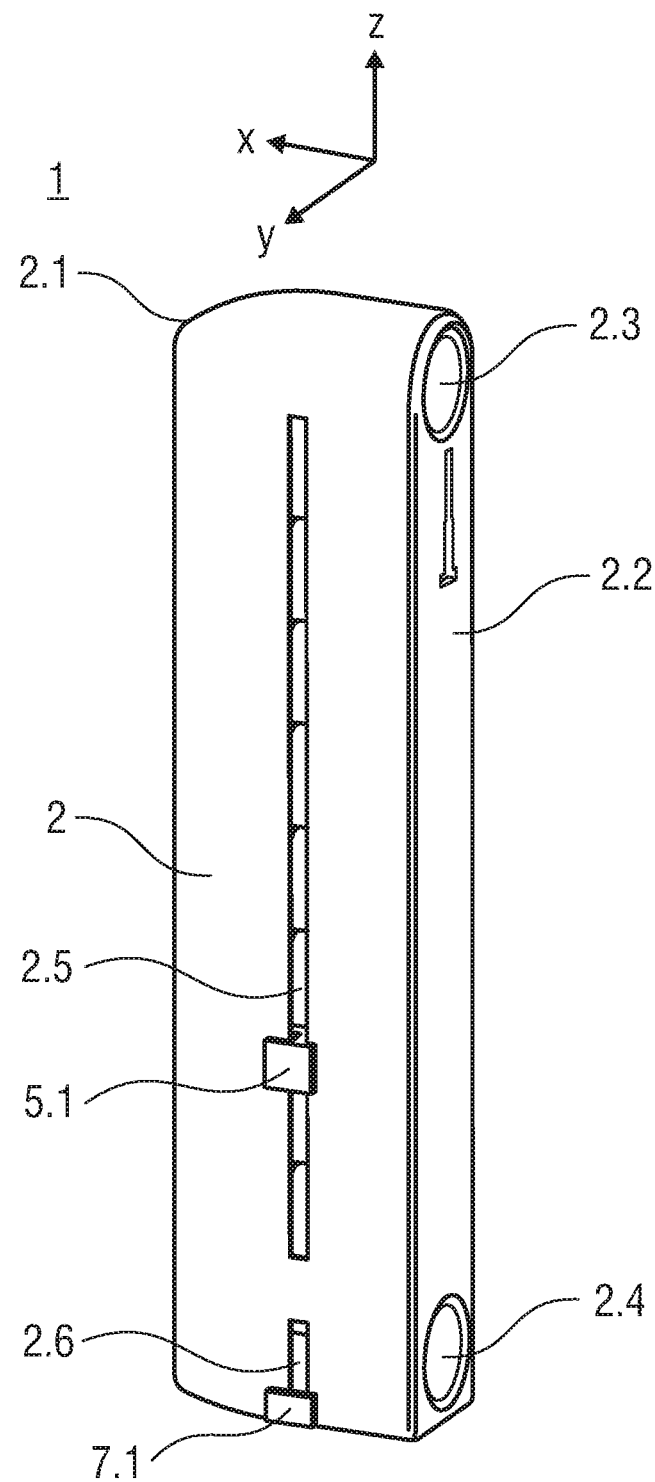
FIG. 1 shows a perspective view of an exemplary embodiment of a needle assembly magazine according to the present invention.
Figure 4:
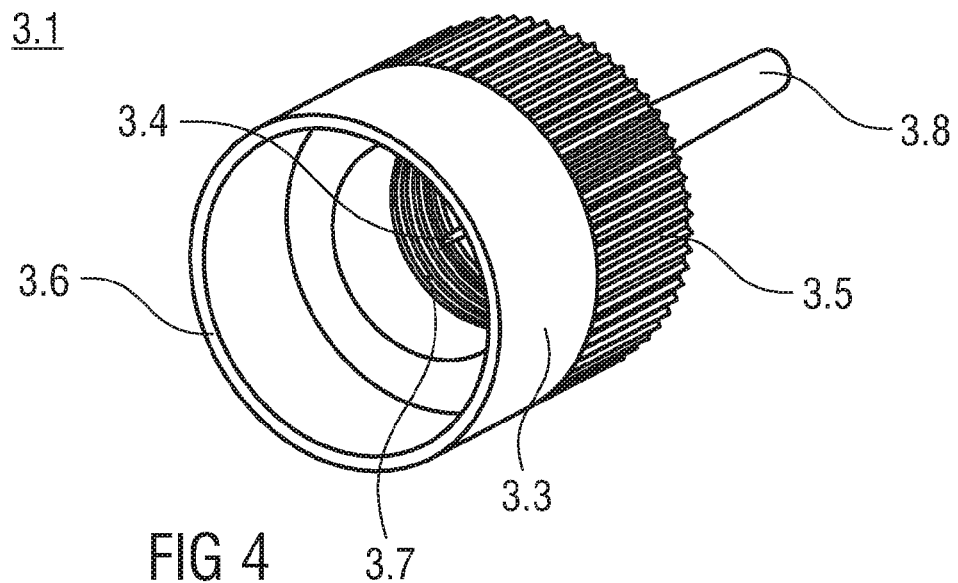
FIG. 4 shows a perspective rear view of an exemplary embodiment of a needle assembly according to the present invention.
Figure 5:
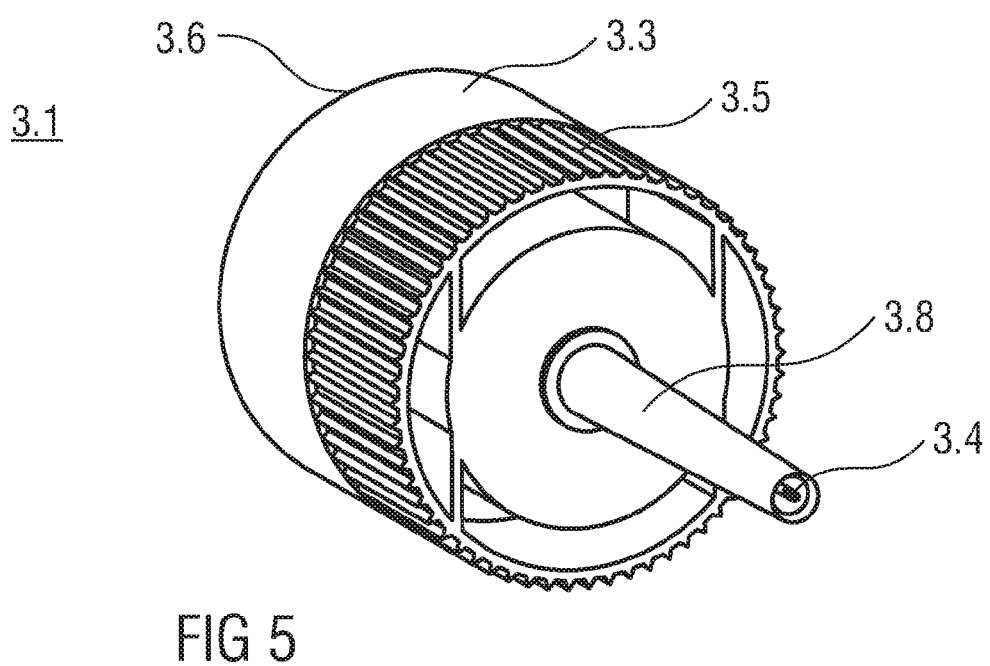
FIG. 5 shows a perspective front view of an exemplary embodiment of a needle assembly according to the present invention.

FIG. 1 shows a perspective view of an exemplary embodiment of a needle assembly magazine 1 for storing a plurality of needle assemblies 3.1, 3.2 (exemplary embodiments of which are shown in FIGS. 4 and 5) according to the present invention. The needle assembly magazine 1 comprises a housing 2 which, in the exemplary embodiment, is an elongated container having a length substantially equal to a sum of diameters of the needle assemblies 3.1 and a width substantially equal to a diameter of one of the needle assemblies 3.1. However, those of skill in the art will understand that a shape and size of the housing 2 may vary based on a number of the needle assemblies 3.1, orientation of the needle assemblies 3.1, size of the needle assemblies 3.1, etc. Generally, the housing 2 may provide a sterile enclosure for the needle assemblies 3.1 and may be manufactured from a material (e.g., rubber, plastic, metal) which will not break or deform when the magazine 1 is transported or dropped.

The housing 2 may be comprised of first and second portions connected by a hinge and a lock, and when the first and second portions are coupled together, a cavity 4 may be formed therein. In this exemplary embodiment, after all of the needle assemblies 3.1 have been used, the housing 2 may be unlocked and opened (e.g., by separating the first and second portions) and the used needle assemblies may be discarded. Unused needle assemblies may then be inserted into the housing 2, and the housing 2 may be locked (e.g., by making the first portion abut the second portion and activating the lock). In another exemplary embodiment, a door may be provided at an end of the housing 2 for replacing the needle assemblies 3.1.

In an exemplary embodiment, the housing 2 may include a first opening 2.3 for dispensing an unused needle assembly and a second opening 2.4 for depositing a used needle assembly. In the exemplary embodiment, the first opening 2.3 is formed at a first terminal end 2.1 of the housing 2, and the second opening 2.4 is formed at a second terminal end of the housing 2. Both of the openings 2.3 and 2.4 may be sized and shaped to receive an injection device (or a distal portion thereof), such as a pen injector, an autoinjector, etc. One or more of the openings 2.3 and 2.4 may be covered by a door, which may be manually moved or automatically moved (e.g., via a spring) to cover/uncover the openings 2.3, 2.4. The first opening 2.3 may include a rim portion or guide 8 formed around the first opening 2.3 which aligns the injection device relative to the unused needle assembly 3.1. A similar rim portion may be formed around the second opening 2.4 to facilitate removal of the used needle assembly.

In an exemplary embodiment, the housing 2 and/or the first and second openings 2.3, 2.4 may be color-coded with different colors to indicate that the first opening 2.3 is for obtaining an unused needle assembly and the second opening 2.4 is for discarding a used needle assembly. The housing 2 may also include labels to indicate the use of each of the openings. For example, a label disposed adjacent the first opening 2.3 may read, "NEW," and a label disposed adjacent the second opening 2.4 may read, "USED."

Figure 2:
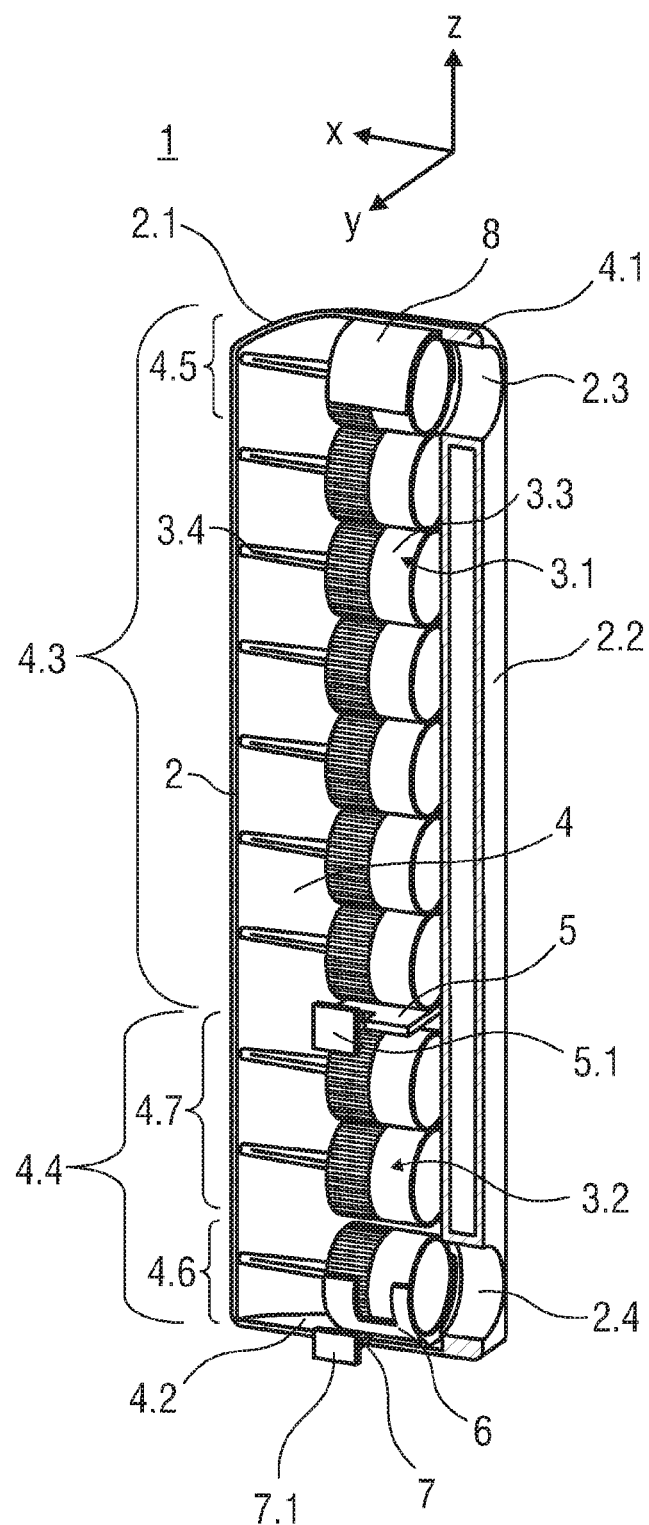
FIG. 2 shows a perspective section view of an exemplary embodiment of a needle assembly magazine according to the present invention.

FIG. 2 shows an exemplary embodiment of the needle assembly magazine 1 according to the present invention. The needle assemblies 3.1 may be maintained in a row due to dimensions of the housing 2. In another exemplary embodiment, consecutive needle assemblies may be coupled to form a strip or array of needle assemblies. In an exemplary embodiment, a coupling between adjacent needle assemblies could be a plastic connector which fractures when a given needle assembly is being rotated to couple to the injection device or upon removal from the housing 2.

In an exemplary embodiment, a slider 5 may be axially movable within the housing 2. In use, the slider 5 can separate the unused needle assemblies (in a first region 4.3) from the used needle assemblies (in a second region 4.4). Prior to use, because all of the needle assemblies 3.1 in the housing 2 are unused, the slider 5 may be positioned near a second end 4.2 of the housing. As needle assemblies 3.1 are removed for use and returned after use, the slider 5 may advance (manually or automatically) through the housing 2 toward a first end 4.1.

In use, the injection device may be inserted into a given needle assembly 3.1 aligned with the first opening 2.3. An area of the housing 2 in which the unused needle assembly 3.1 is aligned with the first opening 2.3 may be referred to as an extraction region 4.5. After the needle assembly 3.1 is removed from the housing 2, the slider 5 may be advanced manually or automatically to align a next unused needle assembly with the first opening 2.3. In an exemplary embodiment, the slider 5 may include a handle 5.1 which projects external to the housing 2 (e.g., through a slot 2.5 formed in the housing 2), allowing for manipulation by the user. After a needle assembly 3.1 has been removed from the housing 2, the slider 5 may be advanced via the handle 5.1 along a length of the housing 2 to move a subsequent needle assembly 3.1 into the extraction region 4.5 and to make room in the housing 2 for return of the needle assembly 3.1 after use. In another exemplary embodiment, the slider 5 may be advanced through the housing 2 automatically, e.g., via a spring. When an unused needle assembly 3.1 is removed from the housing 2, the spring force may advance the slider 5 and push the unused needle assemblies toward the first end 4.1 of the housing 2.1.

An area of the housing 2 in which the used needle assembly 3.1 is deposited into the housing 2 via the second opening 2.4 may be referred to as an insertion region 4.6. The used needle assembly may be inserted into the housing 2 through the second opening 2.4. A holder 6 may be located within the housing 2 internal to the second opening 2.4 to maintain a position of the used needle assembly while it is disconnected from the injection device. For example, the holder 6 may ensure that the used needle assembly does not rotate relative to the injection device. In an exemplary embodiment, the holder 6 may include a pair of arms which at least partially encircle the needle assembly 3.1. The arms may include a textured or frictional surface, or may have a radius of curvature less than a radius of curvature of the needle assembly 3.1, to prevent the needle assembly 3.1 from rotating.

Figure 3:
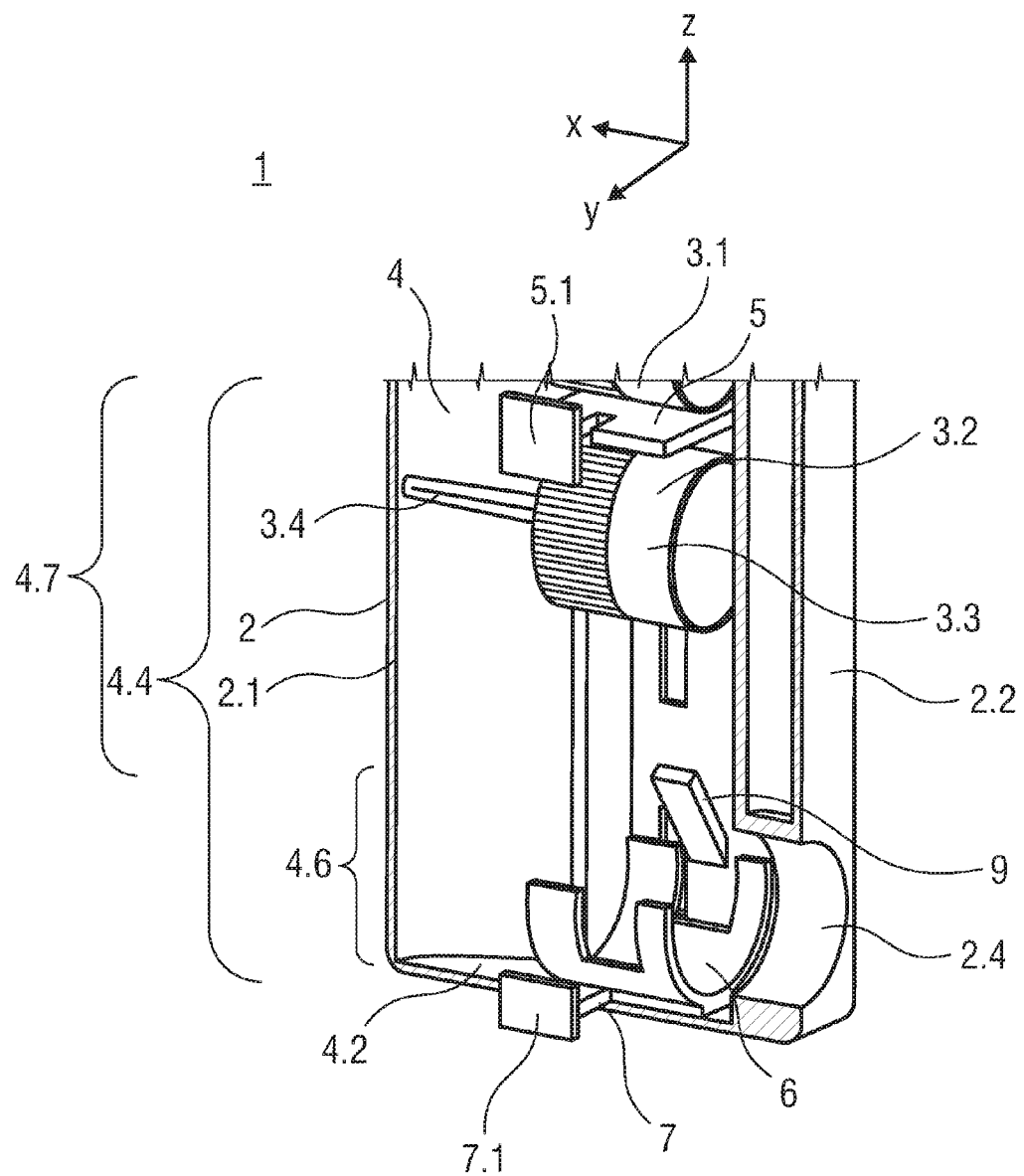
FIG. 3 shows a sectional view of an exemplary embodiment of a needle assembly magazine according to the present invention.

FIG. 3 shows an exemplary embodiment of the second region 4.4 of the needle assembly magazine 1 according to the present invention. When a used needle assembly is inserted into the housing 2 via the second opening 2.4, the holder 6 maintains the used needle assembly is position while it is disconnected from the injection device. After the used needle assembly is disconnected from the injection device, the user may activate a lever 7 which advances the holder 6 toward the first end 4.1. In an exemplary embodiment, the lever 7 projects through a slot 2.6 to an exterior of the housing 2. Activation of the lever 7 advances the holder 6 by a distance substantially equal to a width of a needle assembly. As the holder 6 moves toward the first end 4.1, the holder 6 may deflect a hook 9 formed in the housing 2 and which projects into an interior of the housing 2. The hook 9 may be deflected against an inner surface of the housing 2 to allow the used needle assembly to pass. After the used needle assembly has passed the hook 9, the hook 9 may resiliently return to its original position. The holder 6 may then return to its starting position (e.g., manually or automatically), and as the holder 6 moves toward the second end 4.2, the hook 9 may separate the used needle assembly from the holder 6 and prevent the used needle assembly from moving back to the insertion region 4.6. Thus, the used needle assembly may be maintained in a disposal region 4.7 of the housing 2, between the slider 5 and the insertion region 4.6. The holder 6 may return to its starting position by moving the lever 7 to its starting position, e.g., via a lever handle 7.1. In another exemplary embodiment, the holder 6 may be returned to its starting position automatically, e.g., by a tension spring.

FIGS. 4 and 5 show perspective views a needle assembly 3.1. An outer surface of support 3.3 has a cylindrical shape and an open rear end 3.6. A needle 3.4 (which may include a protective cap 3.8) extends from a distal portion of the support 3.3 along a central axis thereof. The support 3.3 is designed to be mountable on a distal end of an injection device. For this purpose, an inner screw thread 3.7 (or similar coupling mechanism, such as a bayonet or snap fit) may be formed adjacent or on the support 3.3 to mate with a corresponding screw thread on the distal end of the injection device.

In an exemplary embodiment, the inner screw thread 3.7 may be formed distal to the support 3.3, and the support 3.3 may be utilized of aligned the distal end of the injection device with the needle assembly 3.1 for coupling thereto.

A seal may be formed within the support 3.3 to maintain sterility of the needle assembly 3.1. The seal may have perforated edges such that when the injection device is inserted into the needle assembly 3.3, the seal breaks and the injection device has access to the inner screw thread 3.7 and the needle 3.4. The seal may be removed to an area between the support 3.3. and the injection device.

The outer surface of the support 3.3 may have a ring-shaped corrugated region 3.5. The guide 8 and the holder 6 may have corresponding surfaces designed to abut on the corrugated region 3.5 when a needle assembly 3.1 is in the extraction region 4.5 or the insertion region 4.6, thereby providing friction to mount and unmount a needle assembly 3.1 to/from the injection device.

In an exemplary embodiment, the needle assembly magazine 1 includes a container formed therein for storing the protective caps 3.8 of the needle assemblies 3.1 after they are removed from the housing 2. The container may be a pocket formed in the housing 2, and the container may be accessible via a slot. Such a container may be useful if the user is administering an injection in an area (e.g., a camp site) which does not have ready access to trash receptacles.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle assembly magazine comprising:
    a housing adapted to contain a plurality of needle assemblies, the housing having a first opening providing access to an unused needle assembly and a second opening for receiving into the housing a used needle assembly;
    a slider movably disposed within the housing and separating the housing into a first region for unused needle assemblies and a second region for used needle assemblies, wherein movement of the slider advances the unused needle assemblies within the housing toward the first opening;
    a holder disposed within the housing adjacent the second opening, wherein the holder receives the used needle assembly and is movable between a first position and a second position;
    a lever for moving the holder within the housing from the first to the second position; and
    a hook extending into an interior of the housing and separating the used needle assembly from the holder when the holder is moved between the first and second positions.

2. The needle assembly magazine according to claim 1, wherein the housing is elongated.

3. The needle assembly magazine according to claim 1, wherein the housing comprises:
    a first portion;
    a second portion;
    a hinge coupling the first portion to the second portion; and
    a lock for selectively locking the first portion to the second portion.

4. The needle assembly magazine according to claim 1, wherein the first opening is formed at a first terminal end of the housing and the second opening is formed at a second terminal end of the housing.

5. The needle assembly magazine according to claim 1, wherein at least one of the first opening and the second opening is selectively covered by a door.

6. The needle assembly magazine according to claim 1, wherein a guide for an injection device is formed around at least one of the first opening and the second opening.

7. The needle assembly magazine according to claim 1 wherein the holder comprises: a pair of arms adapted to at least partially encircle the used needle assembly.

8. The needle assembly magazine according to claim 1, further comprising:
    a first visual indicator disposed on the housing indicating that the first opening provides access to the unused needle assemblies.

9. The needle assembly magazine according to claim 1, further comprising:
    a second visual indicator disposed on the housing indicating that the second opening is for receiving the used needle assemblies.

* * * * *